United States Patent [19]

Beedle et al.

[11] Patent Number: 5,554,640
[45] Date of Patent: Sep. 10, 1996

[54] USE OF PROPANOLAMINE DERIVATIVES AS SELECTIVE 5-HT$_1$ ANTAGONISTS

[75] Inventors: Edward E. Beedle, Indianapolis; David W. Robertson, Greenwood; David T. Wong, Indianapolis, all of Ind.

[73] Assignee: Eli Lilly and Company, Indianapolis, Ind.

[21] Appl. No.: 385,508

[22] Filed: Feb. 8, 1995

Related U.S. Application Data

[62] Division of Ser. No. 171,943, Dec. 22, 1993, Pat. No. 5,420,294, which is a continuation of Ser. No. 996,484, Dec. 21, 1992, abandoned, which is a continuation of Ser. No. 638,298, Jan. 4, 1991, abandoned, which is a division of Ser. No. 434,137, Nov. 8, 1989, Pat. No. 5,013,761, which is a continuation of Ser. No. 202,767, Jun. 3, 1988, abandoned.

[51] Int. Cl.$^6$ .................... A61K 31/405; A61K 31/135
[52] U.S. Cl. .................... 514/415; 514/424; 514/650; 514/652; 514/653
[58] Field of Search .................... 514/652, 424, 514/653, 415, 650

[56] References Cited

U.S. PATENT DOCUMENTS

| | | | |
|---|---|---|---|
| 3,337,628 | 8/1967 | Crowther et al. | 564/349 |
| 3,415,873 | 12/1968 | Stevens | 564/349 X |
| 3,471,515 | 10/1969 | Troxler et al. | 548/507 X |
| 3,534,086 | 10/1970 | Narayanan et al. | 564/349 X |
| 3,551,493 | 12/1970 | Ruschig et al. | 546/201 X |
| 3,696,120 | 10/1972 | Troxler | 548/503 |
| 4,157,400 | 6/1979 | Mardiguian | 424/330 |
| 4,229,464 | 10/1980 | Kampe et al. | 424/274 |
| 4,304,915 | 12/1981 | Berthold | 546/201 |
| 4,463,190 | 7/1984 | Lunsford et al. | 564/349 |
| 4,564,625 | 1/1986 | Muschaweck et al. | 514/429 |
| 5,013,761 | 5/1991 | Beedle et al. | 514/650 |

FOREIGN PATENT DOCUMENTS

| | | | |
|---|---|---|---|
| 0754360 | 2/1971 | Belgium | 548/503 |
| 5012426 | 12/1975 | Japan | 564/349 |
| 0527188 | 10/1972 | Switzerland | 548/503 |
| 1136919 | 8/1967 | United Kingdom | 564/349 |
| 1079989 | 12/1968 | United Kingdom | 564/349 |
| 93/13049 | 7/1993 | WIPO | 564/349 |

OTHER PUBLICATIONS

Crowther, et al II, *J. Med. Chem.*, 11, 1009–1013 (1968).
Middlemiss I, *Eur. J. Pharmacology*, 120, 51–56 (1986).
Schlicker, et al., *Naunyl–Schmiedeberg's Arch. Pharmacol.*, 331, 398–401 (1985).
Edwards, et al., *Neuropharmacology*, 26 (1), 93–96 (1987).
Maura, et al., *Neuropharmacology*, 26 (7A), 713–717 (1987).
Alexander, et al., *J. Pharm. Pharmacol.*, 39, 664–666 (1987).
Middlemiss II, *Ann. Rept. in Med. Chem.*, 21, 41–50 (1986).
Fuller, *Monographs in Neural Sciences*, 10, 158–181 (1984).
Glennon, *J. Med. Chem.*, 30 (1), 1–12 (1987).
Traber, et al., *TIPS*, 8, 432–437 (1987).
Gorodinskaya I, et al., Chemical Abstracts, 74(3):11638 (1971).
Guzzi, et al., Chemical Abstracts, 114(9):81275 (1989).
Vejdelek, et al., Chemical Abstracts, 113(23):211806 (1990).
Gal, et al., Chemical Abstracts, 103(7):47763 (1985).
Beedle, et al., Chemical Abstracts, 113(1):564 (1988).
Gorodinskaya, Chemical Abstracts, 70(23):104981 (1969).
Crowther, et al. III, Chemical Abstracts, 70(9):37543 (1969).
Simon, et al., Chemical Abstracts, 69:106302 (1968).
Gorodinskaya, et al. II, Chemical Abstracts, 76: 135535 (1972).
Pitah, et al., *J. Med. Chem.*, 30, 612–615 (1987).
Milecki, et al., *J. Med. Chem.*, 30, 1563–1566 (1987).

*Primary Examiner*—Floyd D. Higel
*Attorney, Agent, or Firm*—Joseph A. Jones

[57] ABSTRACT

This invention provides a method of selectively antagonizing the 5-HT$_{1A}$ receptor in mammals by administering aryloxypropanolamines. Aryloxypropanolamines are also claimed.

7 Claims, No Drawings

USE OF PROPANOLAMINE DERIVATIVES AS SELECTIVE 5-HT₁ ANTAGONISTS

This application is a division of application Ser. No. 08/171,943 filed on Dec. 22, 1993, now U.S. Pat. No. 5,420,296, which is a continuation of application Ser. No. 07/996,484, filed on Dec. 21, 1992, now abandoned, which was a continuation of application Ser. No. 07/638,298, filed on Jan. 4, 1991, now abandoned, which is a division of application Ser. No. 07/434,137, filed Nov. 8, 1989, now U.S. Pat. No. 5,013,761, which is a continuation of application Ser. No. 07/202,767, filed Jun. 3, 1988, now abandoned.

BACKGROUND OF THE INVENTION

A variety of compounds are known that affect serotonin receptors. However, only recently has it been appreciated that several recognition sites and subtypes of the serotonin receptor exist—see generally Middlemiss, *Annual Reports of Medicinal Chemistry*, 2.1, 41–50 (Academic Press, 1986) and Glennon, *J. Med. Chem.*, 30(1), 1–12 (1987). For example, compounds known to be selective ligands for the 5-HT₁ receptor have been shown to affect the cardiovascular system, feeding behavior, sexual activity, gastrointestinal function, and body temperature.

Several propanolamines, such as pindolol and propranolol, have been shown to be 5-HT₁ antagonists. However, they are not selective agents for the serotonin receptor due to their β-blocking activities.

It is the purpose of this invention to provide compounds of the propanolamine class having selective 5-HT₁ activity with minimal effects upon the β-receptor.

SUMMARY OF THE INVENTION

This invention provides a method of selectively antagonizing the 5-HT₁ receptor by administering to a manunal all effective antagonizing amount of a compound of the compound of Formula I

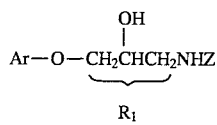

where Ar is

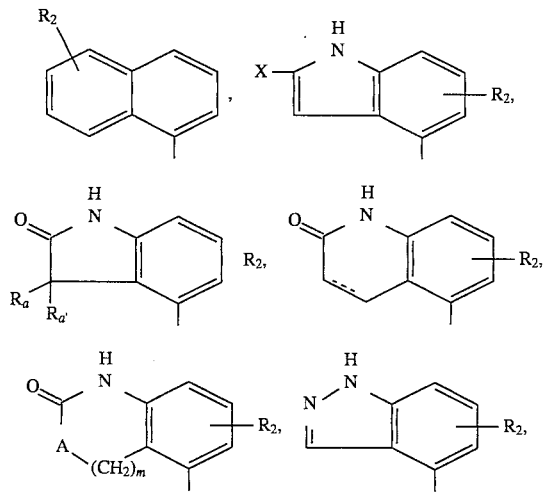

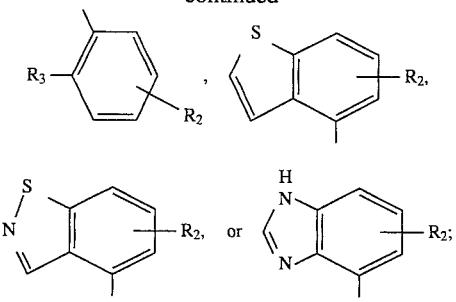

$R_1$ is an optional methyl group substituted on one of the three connecting carbon atoms;

$R_2$ is hydrogen, $C_1$–$C_4$ alkyl, trifluoromethyl, hydroxy, ($C_1$–$C_4$ alkyl)-O-, ($C_1$–$C_4$ alkyl)-S(O)$_p$-, or halo;

$R_3$ is $C_3$–$C_8$ cycloalkyl or a bicycloalkyl group of the formula

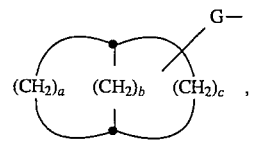

where a and c are independently 1–5, b is 0–5, and (a+c) is greater than 2;

Z is a straight or branched $C_4$–$C_{10}$ alkane, alkene, or alkyne group, ( $C_4$–$C_8$ cycloalkyl ) -G- optionally substituted with $C_1$–$C_4$ alkyl or phenyl, a bicycloalkyl group of the formula

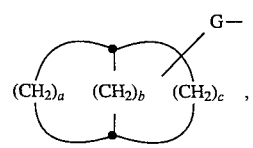

wherein a and c are independently 1–5, b is 0–5, and (a+c) is greater than 2, optionally phenyl substituted $C_2$–$C_{10}$ alkyl where the phenyl group can be optionally substituted with $R_2$ as previously defined, or -($C_1$–$C_4$ alkylidene )-T-($C_1$–$C_4$ alkyl), where T is —O—, —S—, —SO—, or —SO₂—;

where each G is independently a bond or $C_1$–$C_4$ alkylidene;

X is —H, —COY, —CN, or $C_1$–$C_4$ alkyl;

Y is -OH, -O -($C_1$–$C_4$ alkyl), or —NH₂;

――――― represents a single or double bond;

$R_a$ and $R_{a'}$ are independently hydrogen or $C_1$–$C_3$ alkyl, or when taken together with the carbon atom to which they are attached form a $C_3$–$C_8$ cycloalkyl ring;

p is 0, 1, or 2;

A is —O—, —S—, —NH—, or —NCH₃—; and m is 0, 1, 2, or 3;

or a pharmaceutically-acceptable salt thereof.

DETAILED DESCRIPTION AND PREFERRED EMBODIMENT

Although it is known that compounds such as pindolol and propranolol antagonize the 5-HT$_{1A}$ and 5-HT$_{1B}$ receptors, they do so at concentrations far in excess of those shown to block the β-receptor. Accordingly, their usefulness in treating disease states and conditions related to the 5-HT$_1$ receptors are limited.

We have discovered the unexpected finding that extending or otherwise substituting the isopropylamine substituent of such compounds with a longer and/or more sterically hindered substituent on the amine function provides compounds which are much more selective antagonists of the 5-HT$_1$ receptor, i.e., the ratio of concentrations to antagonize the β-receptor compared with the 5-HT$_{1A}$ receptor is at least 1.0. Accordingly, the compounds employed in the present invention should useful for treating a variety of conditions related to the 5-HT$_1$ receptor without the concomitant effects seen with β-blockers. The desired effects seen with the compounds employed in the present invention therefore include treatment of sexual dysfunction, depression, appetite disorders, anxiety, schizophrenia, gastrointestinal disorders, headaches, and cardiovascular disorders.

The term "$C_1$–$C_4$ alkyl" refers to methyl, ethyl, propyl, isopropyl, butyl, sec-butyl, t-butyl, and isobutyl. The term "$C_4$–$C_8$ cycloalkyl" refers to cyclobutyl, cyclopentyl, cyclohexyl, cycloheptyl, and cyclooctyl. Optional substituents on the $C_5$–$C_8$ cycloalkyl ring may be at any position or orientation on the ring other than at the point of attachment to the nitrogen atom.

The term "straight or branched $C_4$–$C_{10}$ alkane" includes alkyl groups of 4–10 carbon atoms as either straight-chain hydrocarbons or with one or more points of branching. Similarly, the term "straight or branched $C_4$–$C_{10}$ alkene or alkyne group" refers to similar straight or branched hydrocarbon chains containing a double or triple bond, respectively. "Halo" refers to fluoro, chloro, bromo, and iodo.

The term "-( $C_1$–$C_4$ alkylidene )-T-($C_1$–$C_4$ alkyl)" refers to two straight or branched $C_1$–$C_4$ alkyl groups bridged by the T functionality. The term "$C_1$–$C_4$ alkylidene" refers to a divalent radical derived from a $C_1$–$C_4$ alkane.

The bicycloalkyl groups defined as part of the $R_3$ and Z substituents include bicyclic rings of four seventeen carbon atoms. These bicycloalkyl groups include bridged and fused two-ring systems. Examples of representative Z substituents are provided in Table I.

The $R_1$ optional methyl group is one wherein the three-carbon bridge between the aryloxy and amine functionalities are optionally substituted with a methyl group. That is, in addition to the —$CH_2CH(OH)CH_2$— bridge as drawn in FIG. 1, such bridging groups also include —CH ($CH_3$) CH (OH) $CH_2$—, —$CH_2C(OH)$ ($CH_3$) $CH_2$—, and —$CH_2CH$ (OH)CH($CH_3$)—.

It is recognized that depending upon the $R_1$, hydroxy, and Z substituent groups, one or more steroisomers and/or enantiomers are possible. This invention is not limited-to any particular isomer but includes all possible individual isomers and all combinations thereof.

The pharmaceutically acceptable addition salts employed in this invention include salts derived from inorganic acids such as hydrochloric acid, nitric acid, phosphoric acid, sulfuric acid, hydrobromic acid, hydriodic acid, phosphorus acid, and the like, as well as salts derived from organic acids, such as aliphatic mono- or di-carboxylic acids, phenyl-substituted alkanoic acids, hydroxy-alkanoic and -alkandioic acids, aromatic acids, aliphatic and aromatic sulfonic acids, and the like.

The preferred compounds employed in this invention are those of the propranolol (Ar=1-naphthyl) and especially the pindolol (Ar=4-indolyl), cyanopindolol (Ar=2-cyano-4-indolyl), and most especially (Ar=2-cyclopentylphenyl) type.

The preferred $R_1$ group is hydrogen, and preferred Z substituents are branched alkyl groups, particularly those of 6–8 carbon atoms, and cyclohexyl, cycloheptyl, cyclooctyl, and bicycloalkyl derivatives.

This invention also provides novel compounds of the above types. The propranolol compounds are represented by Formula Ia

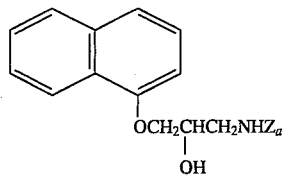

where $Z_a$ is ($C_7$–$C_8$ cycloalkyl)-G- or

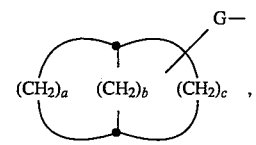

and pharmaceutically acceptable salts thereof.

The pindolol and cyanopindolol compounds are represented by Formula Ib

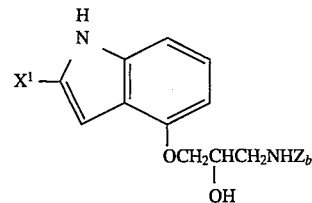

where $X^1$ is hydrogen or cyano and $Z_b$ is ($C_6$–$C_8$ cycloalkyl)-G-, or $C_6$–$C_{10}$ straight or branched alkyl, and pharmaceutically acceptable salts thereof.

Similarly, the penbutolol-type compounds are represented by the Formula Ic

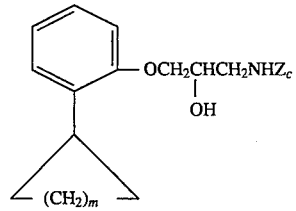

where m is 0–3, especially 2, and $Z_c$ is ($C_6$–$C_8$ cycloalkyl)-G-, $C_6$–$C_{10}$ to alkyl, phenylsubstituted $C_2$–$C_{10}$ alkyl, -($C_1$–$C_4$ alkylidene)-T-($C_1$–$C_4$ alkyl), or

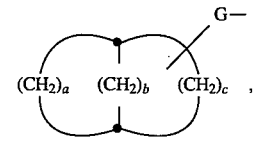

or a pharmaceutically acceptable salt thereof.

The compounds employed in the method of this invention are known in the art or can be prepared by methods known in the art. References illustrative of this chemistry include Crowther et al., *J. Med. Chem.*, 11, 1009 (1968) (propranolol and derivatives ), U.S. Pat. No. 3,551,493 (penbutolol and derivatives), and U. S. Pat. No. 3,471,515 (pindolol and derivatives), which references are expressly incorporated within this application.

In general, the compounds are best prepared according to the following scheme:

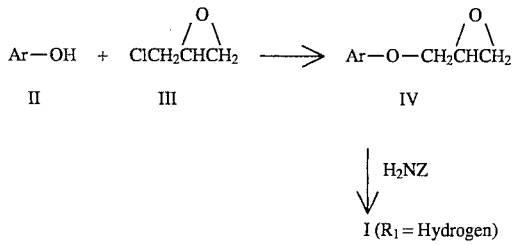

According to Scheme I, the hydroxy aromatic intermediate II is reacted with epichlorohydrin (III) or a halo congener thereof to provide the epoxy derivative IV. This chemistry is well established in the art and can be conducted in a number of ways, generally employing an inert solvent and a nonreactive acid scavenger. Epoxide IV is then reacted with the primary amine $H_2NZ$ to provide the compounds employed in this invention. Once again, the reaction is usually performed in the presence of a nonreactive solvent and at elevated temperatures up to the reflux temperature of the reaction mixture. Scheme I is drawn contemplating those compounds wherein $R_1$ is hydrogen; by employing the appropriately substituted halo epoxide derivative III, the other compounds employed in the present invention may be prepared in a similar manner. The pharmaceutically acceptable salts optionally employed in the present invention may also be prepared by standard methods known to those skilled in the art.

The following Examples are illustrative of the novel and particularly preferred compounds of this invention.

EXAMPLE 1

1-(1-Naphthalenoxy)-3- (cyclooctylamino)-2-propanol ethanedioate

A mixture of 3.17 g of 3-(1-naphthalenoxy)1,2-epoxypropane and 2.01 g of cyclooctylamine were heated to reflux in methanol overnight. The mixture was cooled, concentrated in vacuo, diluted with ethyl acetate and treated with a solution of oxalic acid in ethyl acetate. The resulting precipitate was recovered by filtration and crystallized from ethyl acetate/ diethyl ether to provide 4.3 g of the title product, m.p. 147–148° C.

The following compounds were prepared in similar fashion from the appropriate aryloxy-epoxyropane and corresponding amine:

1-(1-Naphthalenoxy) -3- (cycloheptylamino)-2-propanol ethanedioate, 47% yield, m.p. 161°–162° C., 1-(4- Indolyloxy) -3-(endo-2 -norbornanylamino) -2-propanol ethanedioate, 1-(2-Cyclopentylphenoxy)-3-(cycloheptylamino) 2-propanol ethanedioate, 47% yield, m.p. 192°–194° C., 1-(2-Cyclopentylphenoxy)-3-(cyclooctylamino) 2-propanol ethanedioate, 10% yield, 1-(2-Cyclopentylphenoxy)-3-(1,2,2-dimethyl2-propylamino)-propanol ethanedioate, 9% yield, 1-(2-Cyclopentylphenoxy)-3-(1,1-dimethylbutylamino) -2-propanol ethanedioate, 21% yield, 1-(2-Cyclopentylphenoxy)-3-(myrtanylamino)-2-propanolethanedioate, 1-(4-Indolyloxy)-3-(cyclohexylamino)-2-propanol maleate, 55% yield, m.p. 134–135° C., 1-(2-Cyclopentylphenoxy)-3-cyclohexylamino-2-propanol ethanedioate, 77% yield, m.p. 214–215° C.

The compounds employed in the present invention are antagonists of the serotonin 5-$HT_1$ receptor and have minimal effects upon the β-receptor. The compounds of this invention were evaluated in the following tests systems.

Procedure for radioligand receptor assays—Male Sprague-Dawley rats weighing 110–150 g were decapitated and brains were immediately removed. Bovine brains were quickly removed from calf in the slaughterhouse. Cerebral cortices were dissected out at 4° C. and homogenized in 0.32M sucrose. After centrifugation at 1000×g for 10 minutes and then 17,000×g for 20 minutes, a crude synaptosomal fraction was sedimented. The pellet was suspended in 100 volumes of 50 mM tris-HCl buffered at pH 7.4, incubated at 37° C. for 10 minutes, and centrifuged at 50,000×g for 10 minutes. The process was repeated and the final pellet was suspended in ice-chilled 50 mM tris-HCl buffered at pH 7.4.

Binding of $^3H$-8-hydroxy-2- (di-n-propylamino) tetralin(3H-8OHDPAT) to serotonin-1A receptor was performed according to the method described by Wong et al., *J. Neural Transm.*, 71, 207 (1988). Cortical membranes (300 μg protein) isolated from rat brain were incubated at 28 C for 30 minutes in 2 ml of medium containing 50 mM tris-HCl buffered at pH 7.4; 10 μM pargyline; 0.6 mM ascorbic acid; 5 mM calcium chloride; 0.4 nM 3H-8OHDPAT; and various concentrations of test compound. Binding was terminated by filtering samples under reduced pressure through glass fiber (GFB) filters. The filters were washed twice with 5 ml of ice cold buffer and placed in scintillation vials with 10 ml of PCS (Amlersham/Searle) scintillation fluid. Radioactivity was measured with a liquid scintillation spectrometer. Specific binding of 3H-8OHDPAT is defined as the difference of radioactivity bound in the absence and in the presence of 10 μM spiperone. Concentration of compound required to cause a 50% inhibition ($IC_{50}$ value) of 3H-8OHDPAT binding was computed by linear regression analysis and is reported in Table I as the 5-$HT_{1A}$ $IC_{50}$.

Binding of 3H-dihydroalprenolol to β-adrenergic receptors was conducted according to the method of Wong et al., *Biochemical Pharmacology*, 32(7), 1287 (1983). Cortical membranes (500 μg protein) of calf brain were incubated at 20° C. for 20 minutes in 2 ml of medium containing 50 $mM_4$ tris-HCl buffered at pH 7.4; 2 nM 3H-dihydroalprenolol; and various concentrations of test compound. Binding was terminated by filtering samples through glass fiber (GFC) filters. L-propranolol at 10 μM was included in separate samples to establish nonspecific binding. Other conditions were as described for 3H-8OHDPAT binding. Table I reports the results of this testing as -the beta IC50.

Illustrative compounds of this invention as evaluated in these test systems are reported in Tables I, II, and III. For comparative purposes, the test data for propranolol, i.e., the analogous compound wherein Z is isopropyl, is provided. Also provided is the ratio of the respective $IC_{50}s$.

TABLE I

Effect of Compounds of Formula I to
Antagonize the 5-HT$_{1A}$ and Beta Receptors

[Structure: naphthalene with O-CH$_2$-CH(OH)-CH$_2$-NHZ substituent]

| Z | IC$_{50}$ (nM) 5-HT$_{1A}$ | Beta | Ratio Beta IC$_{50}$/ 5-HT$_{1A}$ IC$_{50}$ |
|---|---|---|---|
| —C(CH$_3$)$_2$CH=CH$_2$ | 100 | 124 | 1.24 |
| —CH(CH$_3$)C≡CH | 180 | 1270 | 7.1 |
| —C(CH$_3$)$_2$C≡CCH$_3$ | 38 | 398 | 10.5 |
| —C(CH$_3$)$_2$C≡CH | 88 | 1358 | 15.4 |
| —C(CH$_3$)$_2$CH$_2$CH$_3$ | 53 | 1046 | 20 |
| —CH$_2$CH$_2$CH$_2$CH$_3$ | 36.9 | 124 | 3.4 |
| —CH$_2$CH$_2$CH$_2$CH$_2$CH$_3$ | 23.4 | 185 | 7.9 |
| —CH$_2$CH(CH$_3$)$_2$ | 73 | 683 | 9.4 |
| —C(CH$_3$)$_2$C(CH$_3$)$_3$ | 16.8 | 225 | 15.2 |
| —(cyclohexyl) | 15.4 | 622 | 40.4 |
| —CH(CH$_3$)C(CH$_3$)$_3$ | 152.3 | 1205 | 7.9 |
| —C(CH$_3$)$_2$CH$_2$CH$_2$CH$_3$ | 41 | 98 | 2.4 |
| —(2-methylcyclohexyl) | 33.4 | 174 | 5.2 |
| —CH(CH$_3$)CH$_2$CH$_3$ | 73 | 104 | 1.4 |
| —(E-4-phenylcyclohexyl) | >1000 | 264 | <0.26 |
| —(Z-4-phenylcyclohexyl) | 34.1 | 442 | 13 |
| —(cyclooctyl) | 45 | 1000 | 22.2 |
| —(cyclopentyl) | 49 | 138 | 2.8 |
| —-(cycloheptyl) | 23 | 2285 | 99 |
| —C(CH$_3$)$_3$ | 77 | 97.3 | 1.3 |
| —CH(CH$_3$)CH$_2$OCH$_3$ | 147 | 65 | 2.3 |
| —CH$_2$CH$_2$C$_6$H$_5$ | 63 | 313 | 4.8 |
| —CH(CH$_3$)$_2$(propranolol) | 100 | 5 | 0.05 |

TABLE II

Effect of Compounds of Formula I to
Antagonize the 5-HT$_{1A}$ and Beta Receptors

[Structure: cyclopentyl-substituted phenyl with OCH$_2$CH(OH)CH$_2$NHZ]

| Z | IC$_{50}$ (nM) 5-HT$_{1A}$ | Beta | Ratio Beta IC$_{50}$/ 5-HT$_{1A}$ IC$_{50}$ |
|---|---|---|---|
| cycloheptyl | 3 | 48 | 16 |
| cyclooctyl | 5 | >1000 | >200 |
| cyclopentyl | 5 | 7 | 1.4 |
| CH(CH$_3$)C(CH$_3$)$_3$ | 13 | 61 | 4.7 |
| CH(CH$_3$)$_2$CH$_2$CH$_2$CH$_3$ | 6.5 | 16 | 2.5 |

TABLE III

Effect of Compounds of Formula I to
Antagonize the 5-HT$_{1A}$ and Beta Receptors

[Structure: indole with OCH$_2$CH(OH)CH$_2$NHZ substituent]

| Z | IC$_{50}$ (nM) 5-HT$_{1A}$ | Beta | Ratio Beta IC$_{50}$/ 5-HT$_{1A}$ IC$_{50}$ |
|---|---|---|---|
| Cyclohexyl | 10.3 | 56 | 5.4 |

As can be discerned from the above test results, those derivatives having longer and/or more branched amino substituents tend to have greater affinity for the 5-HT$_{1A}$ receptor and have increasing selectivity over the β-receptor. For example, in the cycloalkyl series, increasing the ring size from 5 to 6 to 7 carbon atoms results in an increasing ratio of 2.8, 40.4, and 99, respectively. Similarly, those alicyclic substituents which have multiple branching, i.e., contained a plurality of methyl groups off of a straight hydrocarbon, are more potent and have greater selectivity than their non-branched congeners. It is interesting to note that the sec-butyl and isobutyl derivatives described above are 28 and almost 200 times more selective, respectively, than propranolol which is an isopropyl derivative.

Because of their selective affinity for the 5-HT$_{1A}$ receptor, the compounds employed in the present invention should be useful for treating a variety of conditions such as obesity, bulemia, depression, hypertension, aging, memory loss, sexual dysfunction, anxiety, schizophrenia, gastrointestinal disorders, headaches and cardiovascular disorders. To treat such conditions, a typical daily dose will contain a pharmaceutically effective amount of one of the compounds of Formula I. The term "pharmaceutically effective amount", as used herein, represents an amount of a compound of Formula I which is capable of affecting the 5-HT$_{1A}$ receptor in a mammal. The particular dose of a compound administered will, of course, be determined by the particular circumstances surrounding the use, including the specific compound administered, the route of administration, the particular condition being treated, and similar conditions. A typical daily dose will contain from about 0.01 mg/kg to about 20 mg/kg of a compound of Formula I.

The compounds can be administered by a variety of routes including the oral, rectal, transdermal, subcutaneous, intravenous, intramuscular, or intranasal routes. The compounds can be administered in pharmaceutical formulations comprising a compound of Formula I together with one or more pharmaceutically acceptable excipients, diluents, or carriers therefor. Such formulations are well known in this art and can be adapted to provide a unit dosage form depending on the route of administration and other factors as mentioned above.

We claim:

1. A method of selectively antagonizing the 5-HT$_1$ receptor in a mammal comprising administering to a mammal an effective 5-HT$_1$ antagonizing amount of a compound of the formula $$Ar-O-\underbrace{CH_2\overset{OH}{\underset{|}{C}}HCH_2NHZ}_{R_1} \qquad I$$

where Ar is

[chemical structures: substituted naphthyl; indole with X and R$_2$; oxindole with R$_a$, R$_a'$, R$_2$; dihydroquinolinone with R$_2$; benzoxazinone/lactam with A, (CH$_2$)$_m$, R$_2$; indazole with R$_2$; phenyl with R$_2$, R$_3$; benzothiophene with R$_2$; benzisothiazole with R$_2$; or benzimidazole with R$_2$]

R$_1$ is hydrogen or methyl substituted on one of the three connecting carbon atoms;

R$_2$ is hydrogen, C$_1$–C$_4$ alkyl, trifluoromethyl, hydroxy, (C$_1$–C$_4$ alkyl)-O-, (C$_1$–C$_4$ alkyl)-S(O)p-, or halo;

R$_3$ is a bicycloalkyl group of the formula

[bicycloalkyl structure with (CH$_2$)$_a$, (CH$_2$)$_b$, (CH$_2$)$_c$ and G–]

where a and c are independently 1–5, b is 0–5, and (a+c) is greater than 2;

z is a straight or branched C$_4$–C$_{10}$ alkane, alkene, or alkyne group, (C$_4$–C$_8$ cycloalkyl)-G- unsubstituted or substituted with C$_1$–C$_4$ alkyl or phenyl, a bicycloalkyl group of the formula

[bicycloalkyl structure with (CH$_2$)$_a$, (CH$_2$)$_b$, (CH$_2$)$_c$ and G–]

wherein a and c are independently 1–5, b is 0–5, and (a+c) is greater than 2,

C$_2$–C$_{10}$ alkyl unsubstituted or substituted by phenyl which is unsubstituted or substituted by R$_2$ as previously defined, or -(C$_1$–C$_4$ alkylidene)-T-(C$_1$–C$_4$ alkyl), where T is —O—, —S—, —SO—, or —SO$_2$—;

where each G is independently a bond or C$_1$–C$_4$ alkylidene;

X is —H, —COY, —CN, or C$_1$–C$_4$ alkyl;

Y is —OH, —O—(C$_1$–C$_4$ alkyl), or —NH$_2$;

═══ represents a single or double bond;

R$_a$ and R$_a'$ are independently hydrogen or C$_1$–C$_3$ alkyl, or when taken together with the carbon atom to which they are attached form a C$_3$–C$_8$ cycloalkyl ring;

p is 0, 1, or 2;

A is —O—, —S—, —NH—, or —NCH$_3$—; and m is 0, 1, 2, or 3;

or a pharmaceutically-acceptable salt thereof.

2. The method according to claim 1 employing a compound wherein Ar is 1-naphthyl, 4-indolyl, 2-cyano-4-indolyl.

3. The method according to claim 1 employing a compound wherein Z is cyclohexyl, cycloheptyl, cyclooctyl, or C$_6$–C$_8$ alkyl.

4. The method according to claim 2 employing 1-(1-naphthalenoxy)-3-(cyclooctylamino)-2-propanol or a pharmaceutically acceptable salt thereof.

5. The method according to claim 2 employing 1-(1-naphthalenoxy)-3-(cycloheptylamino)-2-propanol or a pharmaceutically acceptable salt thereof.

6. The method according to claim 2 employing 1-(4-indolyloxy)-3-(cycloheptylamino)-2-propanol or a pharmaceutically acceptable salt thereof.

7. The method according to claim 2 employing 1-(4-indolyloxy)-3-(cyclohexylamino)-2-propanol or a pharmaceutically acceptable salt thereof.

* * * * *